US012747904B2

(12) United States Patent
Hanson et al.

(10) Patent No.: US 12,747,904 B2
(45) Date of Patent: Sep. 29, 2026

(54) APPLIANCE AIR FRESHENER

(71) Applicant: Electrolux Home Products, Inc., Charlotte, NC (US)

(72) Inventors: Josh Hanson, Huntersville, NC (US); Ramesh Subramanian, Charlotte, NC (US); Eric Hitchcock, Harrisburg, NC (US); Brent Curtis, Terrell, NC (US); Belinda Zhang, Atlanta, GA (US)

(73) Assignee: Electrolux Home Products, Inc., Charlotte, NC (US)

( * ) Notice: Subject to any disclaimer, the term of this patent is extended or adjusted under 35 U.S.C. 154(b) by 0 days.

(21) Appl. No.: 18/511,805

(22) Filed: Nov. 16, 2023

(65) Prior Publication Data

US 2024/0085084 A1 Mar. 14, 2024

Related U.S. Application Data

(63) Continuation of application No. 16/514,365, filed on Jul. 17, 2019, now Pat. No. 11,859,891.

(51) Int. Cl.

| | |
|---|---|
| ***F25D 17/04*** | (2006.01) |
| ***A61L 9/01*** | (2006.01) |
| ***A61L 9/12*** | (2006.01) |
| ***A61L 9/14*** | (2006.01) |

(52) U.S. Cl.

CPC .............. *F25D 17/042* (2013.01); *A61L 9/12* (2013.01); *A61L 9/01* (2013.01); *A61L 9/14* (2013.01); *A61L 2209/14* (2013.01); *A61L 2209/15* (2013.01); *F25D 2317/0415* (2013.01)

(58) Field of Classification Search

CPC ........... F25D 17/042; F25D 2317/0415; F25D 2317/041; A61L 9/12; A61L 9/01; A61L 9/14; A61L 2209/14; A61L 2209/15

See application file for complete search history.

(56) References Cited

U.S. PATENT DOCUMENTS

| | | | |
|---|---|---|---|
| D312,514 | S | 11/1990 | Thomas |
| 5,352,255 | A | 10/1994 | Taft |
| 5,568,730 | A | 10/1996 | Kim et al. |
| D389,243 | S | 1/1998 | Miller et al. |
| 5,782,944 | A | 7/1998 | Justice |

(Continued)

FOREIGN PATENT DOCUMENTS

| | | | |
|---|---|---|---|
| CN | 103206320 | A | 7/2013 |
| CN | 106377205 | A | 2/2017 |

(Continued)

OTHER PUBLICATIONS

Wikipedia, "Bevel" (Year: 2017).

(Continued)

*Primary Examiner* — Brendan A Hensel
(74) *Attorney, Agent, or Firm* — Banner & Witcoff, Ltd.

(57) ABSTRACT

An appliance air freshener having a frame and an air freshener medium. The frame defines an enclosure having a first face, and a second face opposite and spaced from the first face. The first face and the second face form an outer perimeter of the enclosure. The frame also defines a passage located within and spaced from the outer perimeter and extending along a passage axis from the first face to the second face. The air freshener medium is located within the enclosure.

22 Claims, 9 Drawing Sheets

(56) References Cited

U.S. PATENT DOCUMENTS

| | | | | |
|---|---|---|---|---|
| D402,356 | S | 12/1998 | Hodge | |
| 5,870,945 | A | 2/1999 | Bivens | |
| 6,017,379 | A | 1/2000 | Kauffman | |
| 6,126,707 | A * | 10/2000 | Pitzen | B01D 46/0005 55/497 |
| D438,631 | S | 3/2001 | Miller | |
| D449,878 | S | 10/2001 | Bjersten | |
| 6,412,435 | B1 | 7/2002 | Timmons, Jr. | |
| 6,478,346 | B1 | 11/2002 | Veser et al. | |
| 6,569,219 | B1 | 5/2003 | Connor et al. | |
| 6,860,916 | B2 | 3/2005 | Kubokawa et al. | |
| 6,918,259 | B2 | 7/2005 | Anderson et al. | |
| 6,955,702 | B2 | 10/2005 | Kubokawa et al. | |
| 7,150,774 | B2 | 12/2006 | Kubokawa et al. | |
| 7,169,202 | B2 | 1/2007 | Kubokawa | |
| D538,418 | S | 3/2007 | Pippel et al. | |
| 7,320,719 | B2 | 1/2008 | van de Graaf et al. | |
| 7,335,240 | B2 | 2/2008 | Gunderson et al. | |
| 7,396,375 | B2 | 7/2008 | Nepsund et al. | |
| 7,465,327 | B2 | 12/2008 | Jang et al. | |
| D593,189 | S | 5/2009 | Kawano et al. | |
| D605,274 | S | 12/2009 | Kawano et al. | |
| D605,275 | S | 12/2009 | Kawano et al. | |
| 7,632,340 | B2 | 12/2009 | Brady et al. | |
| 7,641,707 | B2 | 1/2010 | Kang et al. | |
| 7,654,102 | B2 | 2/2010 | Hurlebaus et al. | |
| 7,833,309 | B2 | 11/2010 | Pippel et al. | |
| 7,857,877 | B2 | 12/2010 | Gunderson et al. | |
| D641,461 | S | 7/2011 | Rafi | |
| 7,988,771 | B2 | 8/2011 | Anikhindi et al. | |
| 8,007,572 | B2 | 8/2011 | Gieseke et al. | |
| 8,021,618 | B1 | 9/2011 | Cooper | |
| 8,062,402 | B2 | 11/2011 | Bland, Jr. et al. | |
| D655,802 | S | 3/2012 | Platt | |
| D655,804 | S | 3/2012 | Platt | |
| 8,157,882 | B2 | 4/2012 | Curtis et al. | |
| 8,163,057 | B2 | 4/2012 | Blossey et al. | |
| 8,206,482 | B2 | 6/2012 | Williams et al. | |
| D679,792 | S | 4/2013 | Hollingsworth | |
| 8,557,008 | B2 | 10/2013 | Williams et al. | |
| 8,828,123 | B2 | 9/2014 | Holzmann et al. | |
| D725,254 | S | 3/2015 | Roblin | |
| 9,011,565 | B2 | 4/2015 | Cannon | |
| D732,153 | S | 6/2015 | Sanocki et al. | |
| 9,114,342 | B2 | 8/2015 | Schuld et al. | |
| D754,315 | S | 4/2016 | Morin | |
| 9,345,372 | B2 | 5/2016 | Williams et al. | |
| 9,345,999 | B2 | 5/2016 | McLaurin | |
| D761,407 | S | 7/2016 | Spear | |
| D762,832 | S | 8/2016 | Gale | |
| 9,500,164 | B2 | 11/2016 | Ryon et al. | |
| D775,344 | S | 12/2016 | Wu | |
| 9,510,718 | B2 | 12/2016 | Schultz et al. | |
| D777,237 | S | 1/2017 | Kobayashi | |
| D778,419 | S | 2/2017 | Poindexter | |
| 9,592,463 | B2 | 3/2017 | McLaurin | |
| D783,136 | S | 4/2017 | Park et al. | |
| D787,656 | S | 5/2017 | Yoo et al. | |
| 9,675,225 | B2 | 6/2017 | Williams et al. | |
| 9,700,823 | B2 | 7/2017 | Stoner, Jr. et al. | |
| 9,702,611 | B2 | 7/2017 | Kang et al. | |
| D796,022 | S | 8/2017 | DeChristofaro | |
| 9,726,123 | B2 | 8/2017 | Madeira et al. | |
| 9,776,118 | B2 | 10/2017 | Fedak | |
| D804,005 | S | 11/2017 | Spear | |
| D809,115 | S | 1/2018 | Morin | |
| D814,620 | S | 4/2018 | Mork et al. | |
| 9,932,941 | B2 | 4/2018 | Khami et al. | |
| 10,046,263 | B2 | 8/2018 | Smith et al. | |
| D831,157 | S | 10/2018 | Kronk | |
| 10,087,897 | B2 | 10/2018 | Schultz | |
| 10,139,150 | B2 | 11/2018 | de Cavalcanti et al. | |
| 10,149,586 | B2 | 12/2018 | Liu | |
| 10,239,010 | B2 | 3/2019 | Sang et al. | |
| 10,254,035 | B2 | 4/2019 | Yun et al. | |
| 10,279,298 | B2 | 5/2019 | Sudermann et al. | |
| D852,975 | S | 7/2019 | Jones et al. | |
| 10,384,158 | B2 | 8/2019 | Pflueger et al. | |
| 10,456,725 | B2 | 10/2019 | Kurita et al. | |
| 10,682,597 | B2 | 6/2020 | Krull et al. | |
| D893,695 | S | 8/2020 | Gale et al. | |
| D894,360 | S | 8/2020 | Perez | |
| D910,158 | S | 2/2021 | Kim et al. | |
| D914,864 | S | 3/2021 | Roblin | |
| 10,940,416 | B2 | 3/2021 | Gregerson et al. | |
| 10,981,099 | B2 | 4/2021 | Gregerson et al. | |
| 10,994,235 | B2 | 5/2021 | Zhang et al. | |
| 11,110,382 | B2 | 9/2021 | Burton et al. | |
| 11,123,673 | B2 | 9/2021 | Coulonvaux et al. | |
| 11,260,331 | B2 | 3/2022 | Burton et al. | |
| 11,517,840 | B2 | 12/2022 | Moers et al. | |
| 11,583,795 | B2 | 2/2023 | Rauschmaier et al. | |
| D992,714 | S | 7/2023 | Bridgemohan | |
| D998,126 | S | 9/2023 | Gregerson et al. | |
| D998,923 | S | 9/2023 | Qiu et al. | |
| 2008/0064319 | A1 | 3/2008 | Chezick | |
| 2009/0183473 | A1 | 7/2009 | Hui | |
| 2010/0218468 | A1 * | 9/2010 | Curtis | B01D 46/0036 55/357 |
| 2015/0060565 | A1 * | 3/2015 | Furner | A01M 1/02 239/34 |
| 2016/0108866 | A1 | 4/2016 | Dewit et al. | |
| 2016/0131094 | A1 | 5/2016 | Pereira Madeira et al. | |
| 2017/0007951 | A1 | 1/2017 | deChristofaro | |
| 2017/0328315 | A1 | 11/2017 | Sullivan et al. | |
| 2017/0336128 | A1 | 11/2017 | de Cavalcanti et al. | |
| 2018/0272263 | A1 | 9/2018 | Gregerson et al. | |
| 2018/0296962 | A1 | 10/2018 | Sang et al. | |
| 2018/0326342 | A1 | 11/2018 | Smith et al. | |
| 2019/0041117 | A1 | 2/2019 | de Cavalcanti et al. | |
| 2020/0030470 | A1 * | 1/2020 | Mauzerall | A61L 2/07 |
| 2020/0164298 | A1 | 5/2020 | Drabek et al. | |
| 2020/0297886 | A1 * | 9/2020 | Uesugi | B01J 20/3246 |

FOREIGN PATENT DOCUMENTS

| | | | |
|---|---|---|---|
| DE | 19824506 | C1 | 7/1999 |
| DE | 10134545 | A1 | 2/2003 |
| DE | 102007021568 | A1 | 11/2008 |
| DE | 102009015095 | A1 | 10/2010 |
| DE | 102009015097 | A1 | 10/2010 |
| DE | 102014016672 | A1 | 5/2015 |
| EP | 0933600 | A2 | 8/1999 |
| EP | 1591733 | A1 | 11/2005 |
| EP | 1800729 | B1 | 6/2010 |
| EP | 1525043 | B1 | 9/2010 |
| EP | 2516037 | B1 | 2/2014 |
| EP | 2344267 | B1 | 5/2014 |
| EP | 2801733 | A1 | 11/2014 |
| EP | 2833088 | A2 | 2/2015 |
| JP | 11-76728 | A | 3/1999 |
| JP | 2003148861 | A | 5/2003 |
| JP | 2015208701 | A | 11/2015 |
| RU | 2306186 | C1 | 9/2007 |
| RU | 2333029 | C1 | 9/2008 |
| WO | 2018086281 | A1 | 5/2018 |

OTHER PUBLICATIONS

Oct. 27, 2022—(US) Non-Final Office Action—U.S. Appl. No. 16/514,365.
Apr. 25, 2023—(US) Final Office Action—U.S. Appl. No. 16/514,365.
Pages from Universal Appliance Installation Parts & Accessories 2019 Catalog (prior to Jul. 17, 2019).
Statement Accompanying Sep. 25, 2023, IDS.

* cited by examiner

APPLIANCE AIR FRESHENER

CROSS-REFERENCE TO RELATED APPLICATION

This application is a continuation of U.S. patent application Ser. No. 16/514,365, titled "Appliance Air Freshener" and filed Jul. 17, 2019(now U.S. Pat. No. 11,859,891). U.S. patent application Ser. No. 16/514,365, in its entirety, is incorporated by reference herein.

TECHNICAL FIELD

This invention relates to air fresheners for use in appliances and other closed environments, such as refrigerators, freezers, and other enclosed spaces.

BACKGROUND

Various kinds of appliances are equipped with air filtration or air freshening systems to reduce odors that might be present during operation of the device. For example, refrigerators and freezers are sometimes equipped with active air cleaning systems to circulate and filter the air within the appliance cabinets. As another example, it is known to place open containers of sodium bicarbonate or other chemicals in a refrigerator cabinet to passively reduce odors without the need for an air flow generating system to move the affected air through a filtration/odor reducing system.

Some appliances have built-in provisions for holding a passive air freshener. For example, it is known to provide refrigerators with a small compartment that receives a replaceable air freshener.

Air fresheners can use a variety of different chemical compositions to reduce or mask odors. Sodium bicarbonate and activated carbon are two examples of chemicals that are useful for this purpose. Air fresheners also may include odorants, such as fragrances that cover undesirable odors. Air fresheners also sometimes include both an odor-reducing compound, and a fragrance to replace the removed odors.

This description of the background is provided to assist with an understanding of the following explanations of exemplary embodiments, and is not an admission that any or all of this background information is necessarily prior art.

SUMMARY

In a first aspect, there is provided an appliance air freshener having a frame and an air freshener medium. The frame defines an enclosure having a first face, and a second face opposite and spaced from the first face. The first face and the second face form an outer perimeter of the enclosure. The frame also defines a passage located within and spaced from the outer perimeter and extending along a passage axis from the first face to the second face. The air freshener medium located within the enclosure.

In some aspects, the first face extends in a first plane, the second face extends in a second plane, and the first plane and the second plane are parallel to one another.

Some aspects further include a sidewall extending from the first face to the second face at the outer perimeter of the enclosure. The outer perimeter may be elongated in a longitudinal direction, and the sidewall may have a first end wall at first end of the outer perimeter in the longitudinal direction, and a second end wall at a second end of the outer perimeter in the longitudinal direction. Each of the first end wall and the second end wall may have a concave curved outer surface as viewed along the passage axis. The air freshener medium may include a pleated sheet having a plurality of pleats folded in a direction perpendicular to the longitudinal direction. The sidewall may have one or more openings through the frame.

In some aspects, the first face and the second face each have one or more respective openings through the frame.

In some aspects, the air freshener medium may be a pleated sheet having an opening surrounding the passage.

In some aspects, the frame is a unitary plastic structure.

In some aspects, the frame is a folded sheet structure.

In some aspects, the frame has a housing portion and a lid portion that are configurable between a closed position in which the housing portion and the lid portion form the enclosure and the air freshener medium is retained in the enclosure, and an open position in which the freshener medium is removable from the enclosure. The frame may be a unitary plastic structure, with the housing portion attached to the lid portion by a unitary hinge.

In some aspects, the passage is attached to the outer perimeter of the enclosure by one or more ribs. The one or more ribs may be located on the first face, with no ribs are located on the second face. The outer perimeter may have four sides as viewed along the passage axis, and the one or more ribs may extend from a midpoint of each of the four sides to the passage.

In some aspects, the passage is located at a geometric center of the outer perimeter.

In some aspects, the passage has a first perimeter portion and a second perimeter portion facing and parallel to the first perimeter portion. The first perimeter portion and second perimeter portion may be opposite sides of a rectangular perimeter surface.

In some aspects, the passage extends from a first opening at the first face to a second opening at the second face. The first opening may have a perimeter having at least two first points positioned on a first line, and at least two second points positioned on a second line that is parallel to and spaced from the first line.

In some aspects, the passage comprises a first portion permanently secured to the first face and a second portion permanently secured to the second face, and a connector joins the first portion to the second portion.

In another exemplary aspect, there is provided an appliance air freshener system having a frame, an air freshener medium, and a cover. The frame defines an enclosure having a first face and a second face opposite and spaced from the first face, a sidewall extending between the first face and the second face and forming an outer perimeter of the enclosure, and a passage located within the outer perimeter and extending along a passage axis from the first face to the second face. The air freshener medium is located within the enclosure. The cover has a cover body that is larger than the outer perimeter of the enclosure, and one or more posts extending from the cover body and configured to install into the passage to secure the frame to the cover.

In some aspects, the outer perimeter of the enclosure is elongated in a longitudinal direction, and the sidewall has a first end wall at first end of the outer perimeter of the enclosure in the longitudinal direction, and a second end wall at a second end of the outer perimeter of the enclosure in the longitudinal direction. The cover may have a first protrusion extending from the cover body adjacent the first end wall and a second protrusion extending from the cover body adjacent the second end wall when the frame is secured to the cover. Each of the first end wall and the second end wall may have a respective concave curved outer surface as viewed along the passage axis, and each of the first protrusion and the second protrusion may be located within a respective concavity formed by the respective concave curved outer surface of the first end wall and the second end wall when the frame is secured to the cover.

In some aspects, the passage includes a first perimeter portion and a second perimeter portion facing and parallel to the first perimeter portion, and the one or more posts include a first post that is positioned adjacent the first perimeter portion and a second post that is positioned adjacent the second perimeter portion when the frame is secured to the cover.

In some aspects, the passage extends from a first opening at the first face to a second opening at the second face, and the first opening comprises a first beveled entryway extending towards the second face and the second opening comprises a second beveled entryway extending towards the first face. The one or more posts may have a first post having a first hook extending laterally from the first post, and a second post having a second hook extending laterally from the second post, the first hook and the second hook extending in opposite directions and being positioned to engage the first beveled entryway when the frame is secured to the cover with the second face facing the cover, and positioned to engage the second beveled entryway when the frame is secures to the cover with the first face facing the cover. At least one of the first hook and the second hook may have a beveled surface facing the first beveled entryway when the frame is secured to the cover with the second face facing the cover, and facing the second beveled entryway when the frame is secure to the cover with the first face facing the cover.

In some aspects, the one or more posts include two posts, each post having a respective snap fit connector extending in a direction opposite the other snap fit connector.

In some aspects, the passage and one or more posts are configured to selectively and interchangeably secure the frame to the cover body with the first face facing the cover body or the second face facing the cover body.

In some aspects, the cover has one or more connectors configured to secure the cover to a surface with the frame located between the cover body and the surface.

In another exemplary embodiment, there is provided an air freshener element having a body comprising one or more odor-reducing compounds or fragrance-emitting compounds. The body has a rectangular outer perimeter, and an opening at a geometric center of the rectangular outer perimeter.

In some aspects, the body is a pleated sheet.

BRIEF DESCRIPTION OF THE DRAWINGS

Embodiments of inventions will now be described, strictly by way of example, with reference to the accompanying drawings, in which.

DESCRIPTION OF EXEMPLARY EMBODIMENTS

The inventors have found that existing air freshening systems for appliances continue to need improvement. The following embodiments are examples of air freshener systems that are intended for use in appliances, such as refrigerators and freezers. However, it will be appreciated that such air freshener systems can be readily adapted for use in other enclosed spaces, such as automobile cabins, rooms, and so on.

Figure 2:
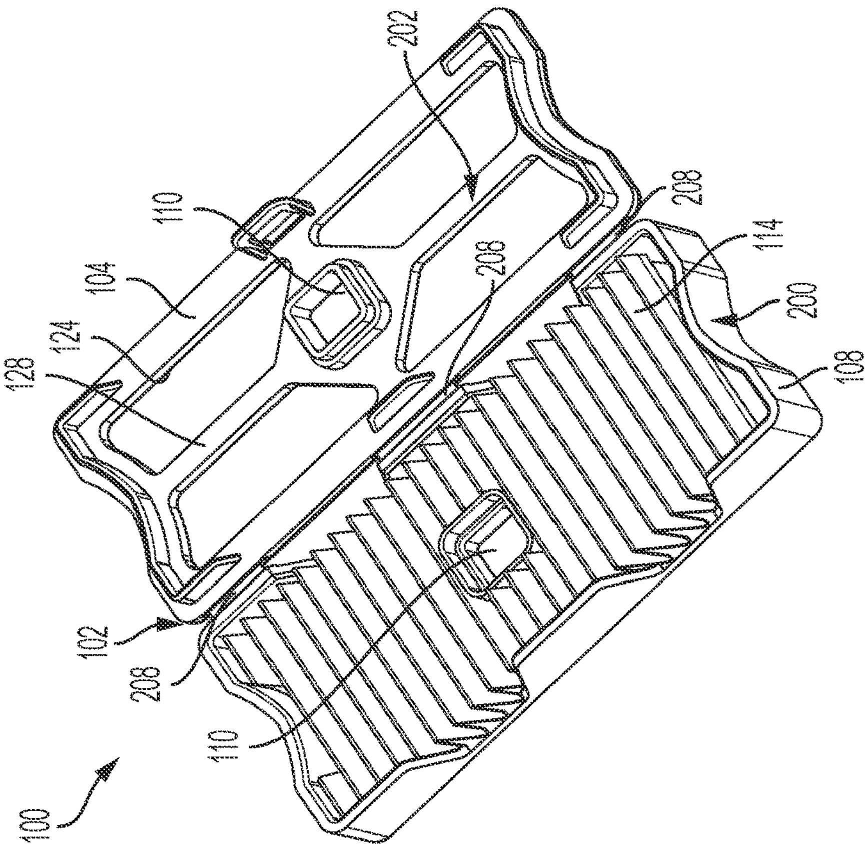
FIG. 2 shows the embodiment of FIG. 1 with a cover portion opened.
Figure 1:
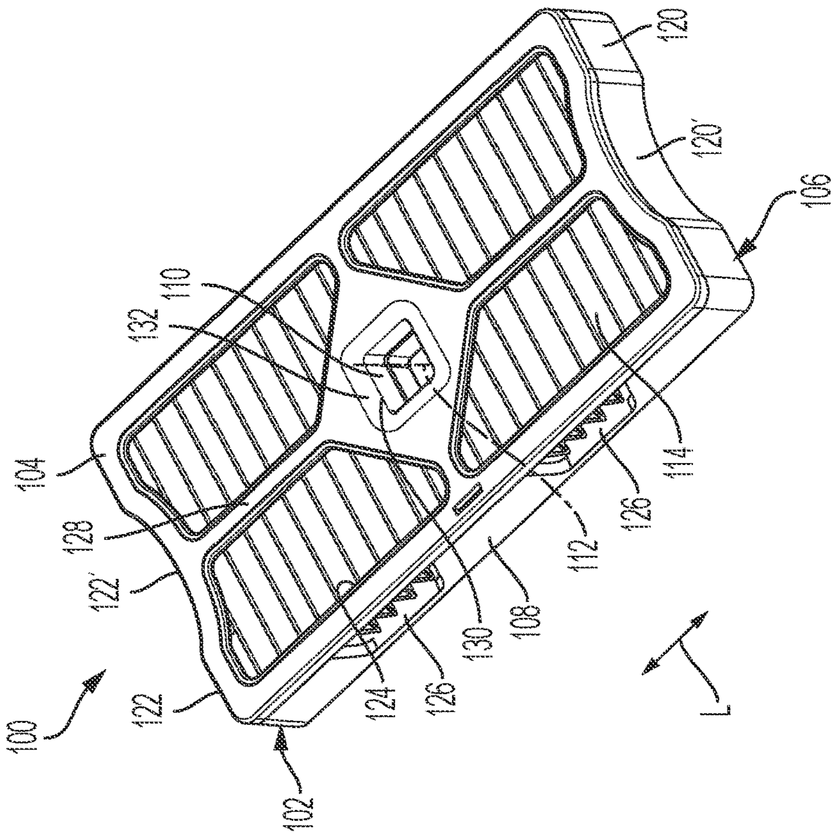
FIG. 1 is an isometric view of an exemplary embodiment of an air freshener.
Figure 3:
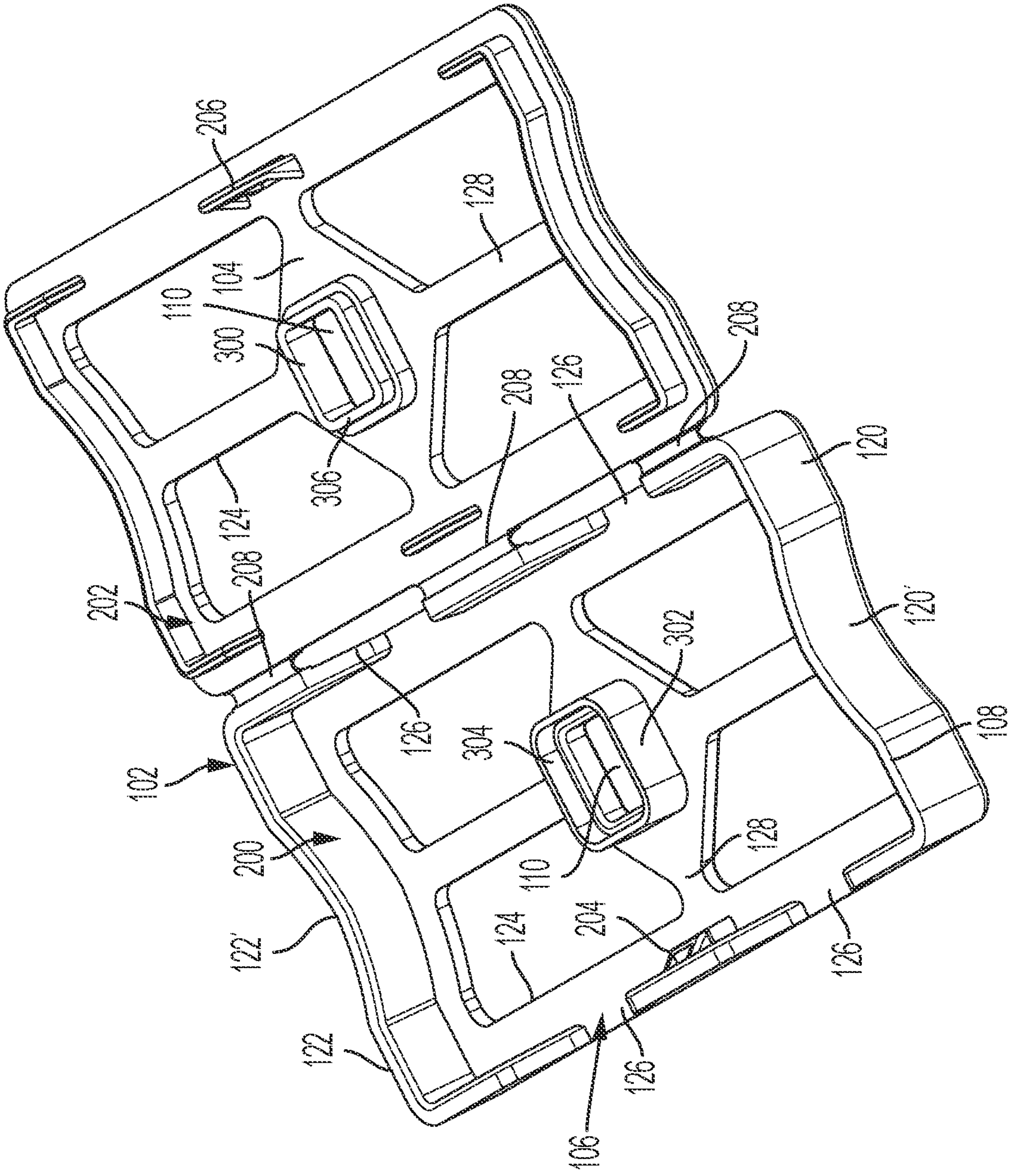
FIG. 3 shows the embodiment of FIG. 1 with a cover portion opened and the air freshener medium removed.

FIGS. 1-3 illustrate a first embodiment of an air freshener 100. The air freshener includes a frame 102 that defines an enclosure having a first face 104, a second face 106 opposite and spaced from the first face 104, and sidewall 108 extending between the first face 104 and the second face 106. The sidewall 108 forms an outer perimeter of the enclosure. A passage 110 is located within the outer perimeter and extends along a passage axis 112 from the first face 104 to the second face 106. An air freshener medium 114 is located within the enclosure.

The frame 102 may be formed of plastic, metal, paper, or other suitable materials. In this example, the frame 102 comprises a plastic material, such as polyethylene, propylene, polyvinyl chloride, polylactic acid, or acrylonitrile butadiene styrene. The frame may be formed by injection molding or other known processes.

The air freshener medium 114 may comprise any chemical or chemicals that help reduce some odors or generate other odors. For example, the air freshener medium 114 may comprise a mix of one or more of: sodium bicarbonate, activated charcoal, and fragrance-emitting compounds. More details of exemplary air freshener media 114 are discussed below.

In the shown example, the frame 102 forms a flat enclosure, in which the first face 104 extends in a first plane, and the second face 106 extends in a second plane, with the second plane being parallel to and spaced from the first plane. Thus, the first face 104 and second face 106 are flat and parallel to one another, giving the frame 102 a flat appearance. In other embodiments, the first face 104 and second face 106 may have different shapes or different curvatures. For example, the first face 104 and second face 106 may comprise flat faces that are not parallel to one another. As another example, one or both of the first face 104 and the second face 106 may have a curved shape, such as a cylindrical or spherical shape.

The sidewall 108 extends from the first face 104 to the second face 106, and connects the first face 104 to the second face 106 at one or more locations around the perimeter of the enclosure. The sidewall 108 may be integrally formed with one or both of the first face 104 and the second face 106. In this case, the sidewall 108 is integrally formed with the second face 106 to form a housing portion 200 of the frame 102, and the first face 104 is formed as a lid portion 202 of the frame 102. The housing portion 200 and lid portion 202 may be configurable between a closed position (FIG. 1) in which the housing portion 200 and lid portion 202 form an enclosure that retains the air freshener medium 114, and an open position (FIG. 2) in which the air freshener medium 114 may be removed from the frame 102 for cleaning or replacement. In this case, a latch mechanism may be provided to secure the housing portion 200 and the lid portion 202 in the closed position. Any suitable latch may be used, such as a protrusion 204 on the housing portion 200 that snaps into a ledge 206 on the lid portion. Alternatively, the housing portion 200 and lid portion 202 may be permanently connected, such as by molding them as a single integral part, or by sealing them together using ultrasonic bonding, adhesives, or the like.

The frame 102 may comprise multiple separate parts that are connected together, or a unitary structure. In the shown embodiment, the housing portion 200 and lid portion 202 are formed as a single plastic molding, in which the housing portion 200 and lid portion 202 are connected to one another by one or more unitary hinges 208. The hinges 208 are molded in place and flexible enough to allow the housing portion 200 and lid portion 202 to move between the open position and the closed position. If the frame is made of multiple parts, the hinge 208 can be eliminated or replaced with a mechanical hinge, such as a pivot pin connection. Other alternatives and variations will be apparent to persons of ordinary skill in the art in view of the present disclosure.

The outer perimeter of the enclosure may have any suitable shape (e.g., oval, circular, square, triangular, rectangular, etc.). In the shown example, the outer perimeter is elongated along a longitudinal direction L to form a rectangular shape as viewed along the passage axis 112. The sidewall 108, which is located at the outer perimeter, includes a first end wall 120 at a first longitudinal end of the outer perimeter, and a second end wall 122 at a second longitudinal end of the outer perimeter. The first and second end walls 120, 122 may be straight and parallel to one another. In the shown example, each end wall 120, 122 comprises a respective curved outer surface 120', 122', and each curved outer surface 120', 122' is concave (i.e., bowed inwards towards the center of the frame 102) as viewed along the passage axis 112. The frame 102 may be dimensioned such that the concave curved outer surface 120', 122' are sized to be grasped by the finger and thumb of a user's hand (e.g., about 3" to 5" apart at their nearest points). The outer surfaces 120', 122' also may include ridges or textured surfaces to assist the user with grasping the frame 102. Other embodiments may have significantly different dimensions. For example, the enclosure may be extended along the longitudinal direction L, and in width and thickness directions perpendicular to the longitudinal direction L. If the length in the longitudinal direction L exceeds a distance that allows a user to grasp the end walls 120, 122, then the longitudinal sidewalls may be shaped with recesses or the like to accommodate a user's fingers, or they may simply be flat. In other cases, specific grasping features such as the curved outer surfaces 120', 122' may be omitted entirely. Also, in embodiments in which the size of the frame 102 is potentially too great to be retained by a single mounting passage 110, multiple passages may be provided. Other alternatives and variations will be apparent to persons of ordinary skill in the art in view of the present disclosure.

The frame 102 includes one or more openings through which ambient air can pass to reach the air freshener medium 114. For example, the first face 104 and second face 106 each may include one or more openings 124. The sidewall 108 also may include one or more openings 126. Furthermore, the frame 102 may be removed from one or more of the first face 104, the second face 106 or the sidewall 108 to provide a larger air passage. For example, the first face 104 and second face 106 may be connected to one another by the passage 110 or the air freshener medium itself, thus eliminating the need for any sidewall 108 structure surrounding the enclosure.

In the example of FIGS. 1-3 the first face 104 and second face 106 each comprise four openings 124. The openings 124 are arranged in respective quadrants of the rectangular frame 102, and separated from one another by ribs 128. The ribs 128 extend from the outer perimeter of the frame 102 and enclosure to the passage 110, and provide support to hold the passage 110 in a fixed position relative to the rest of the frame 102. Each rib 128 may extend from a midpoint of each of the four sides of the rectangular perimeter to connect to the passage 110. In this case, the passage 110 is located at the geometric center of the outer perimeter of the enclosure. In other cases, different arrangements and numbers of ribs 128 may be used, and the passage 110 may be located offset from the geometric center of the outer perimeter of the enclosure.

The passage 110 may be formed in various ways. In one example, the passage 110 may comprise only a first opening through the frame 102 at the first face 104, and a second opening through the frame 102 at the second face 106. In this case, the passage 110 extends along the passage axis from the first face 104 to the second face 106, but the two openings are not directly connected to one another by a passage structure. More preferably, and as best shown in FIG. 3, the passage 110 may comprise a first passage portion 300 extending from the frame 102 at the first face 104, and a second passage portion 302 extending from the frame 102 at the second face 106. The first passage portion 300 and the second passage portion 302 are dimensioned to contact one another to form a continuous closed passage 110 when the housing portion 200 and the lid portion 202 are in the closed position. Alternatively, one of the first passage portion 300 and the second passage portion 302 may be omitted, and the other extended to reach all the way to the frame 102 at the opposite side of the enclosure when the parts are in the closed position.

A latching mechanism may be provided to secure the first passage portion 300 directly to the second passage portion 302. For example, the first passage portion 300 may include a male snap fit connector 306, and the second passage portion 302 may include a female snap fit connector 304 that resiliently engages the male snap fit connector 306 when the parts are in the closed position. The snap fit connectors 304, 306 secure the first face 104 to the second face 106 via the structure of the passage 110. Such snap fit connectors 304, 306 may be releasable to open the enclosure, or permanently engaged (i.e., cannot be separated without damaging the parts). In other embodiments, there may be no latching mechanism, or the first and second passage portions 300, 302 may be retained together loosely be slip-fit portions. In still other embodiments, the first and second passage portions 300, 302 may be permanently connected by adhesives, ultrasonic welding, or the like.

The first passage portion 300 and second passage portion 302 may be integrally formed with the housing portion 200 and lid portion 202 of the frame 102, respectively, making them permanently attached to the underlying structure. Alternatively, one or both of the first passage portion 300 and the second passage portion 302 may be formed separately and attached, either permanently or removably, to the remainder of the frame 102. In still other embodiments, such as those in which the frame 102 comprises a single unitary structure, the passage 110 may comprise a unitary passage extending from the opening at the first face 104 to the opening at the second face 106. Other alternatives and variations will be apparent to persons of ordinary skill in the art in view of the present disclosure.

Figure 4A:
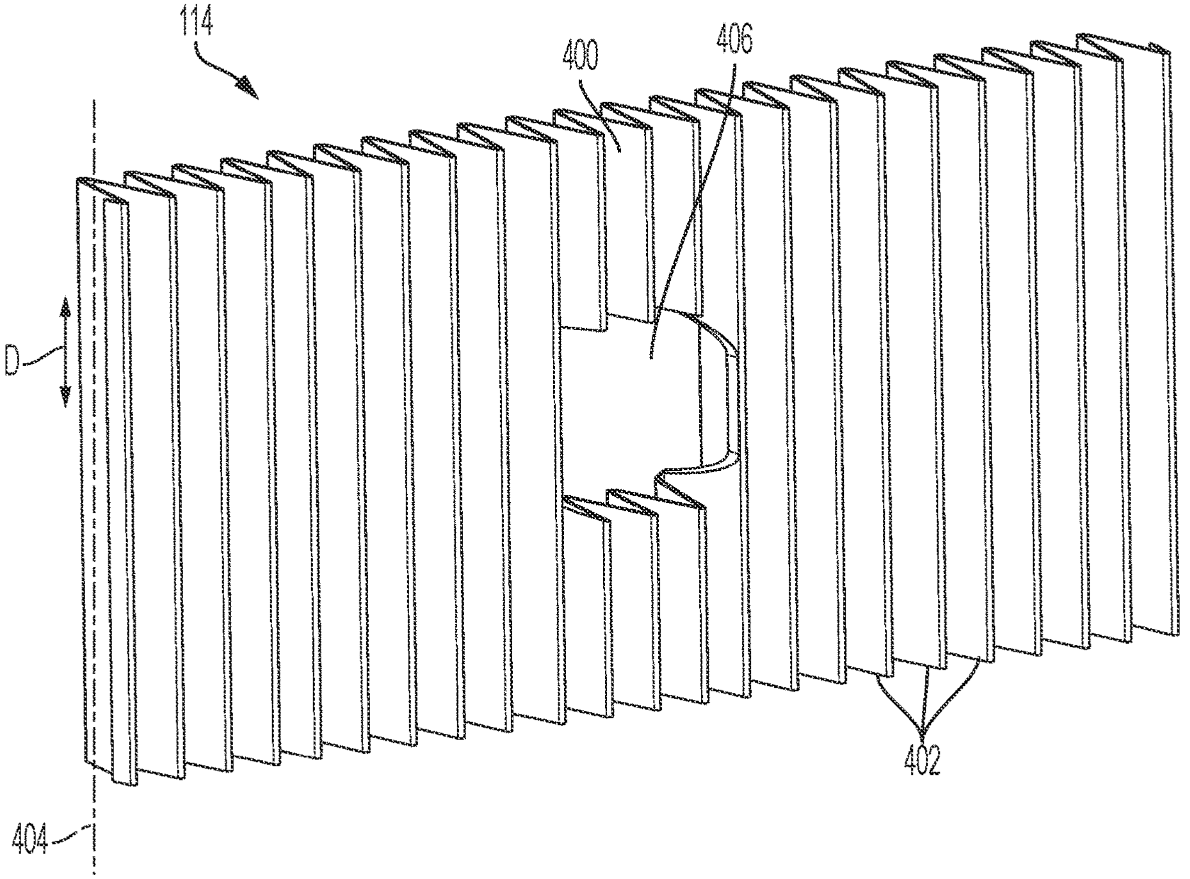
FIGS. 4A and 4B show exemplary embodiments of an air freshener medium.
Figure 4B:
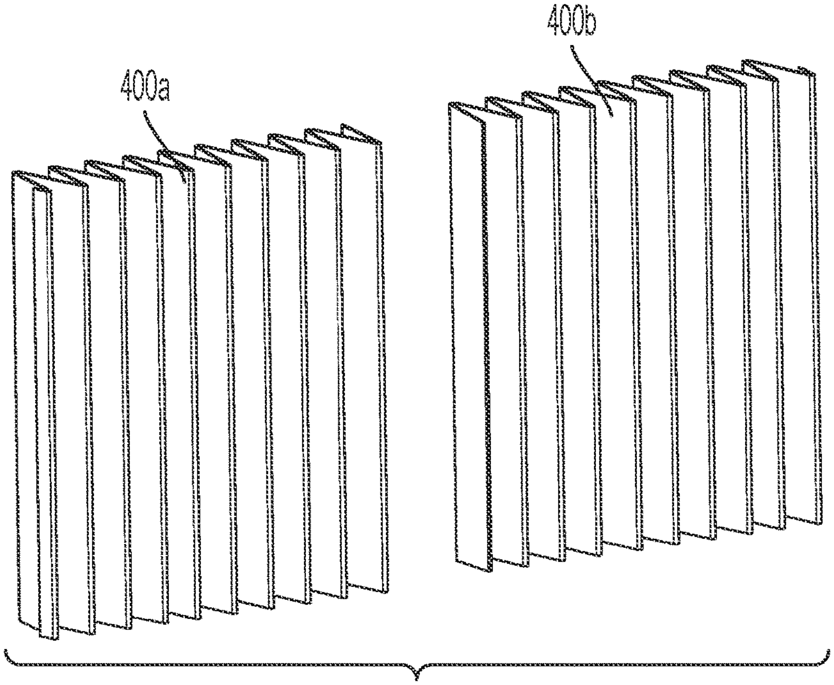

Referring now also to FIGS. 4A and 4B, the air freshener medium 114 may be provided in any suitable physical form. For example, the air freshener medium 114 may comprise a pleated sheet 400 of nonwoven or woven paper or fabric having odor neutralizing or fragrance compounds impregnated into the sheet 400. The pleats 402 comprise folds in the sheet 400, with all of the pleats 402 preferably being folded in the same direction. As used herein, the direction of the fold is direction parallel to the axis about which the fold is made. The folding axis 404 for one pleat 402 is illustrated in FIG. 4A, and the folding direction is shown by arrow D. Other embodiments may have pleats folded in different directions, such as in a radial pattern. Pleats 402 increase the surface area of the air freshener medium 114 relative to a flat sheet of material bounded by the same perimeter, thus enhancing the amount of odor neutralizing capacity of the air freshener medium 114.

The folding direction D may be selected to obtain certain benefits. For example, in an embodiment in which the frame 102 forms an elongated enclosure (e.g., rectangular or oval), the folding direction D may be oriented perpendicular to the longitudinal direction L of the frame 102, such as shown in FIG. 1. In this configuration, and the orientation of the pleats 402 creates relatively short passages along the lengths of the pleats 402 to minimize the distance the air must travel to reach the inner portions of the air freshener medium 114.

In addition, the frame 102 may be configured to better facilitate air interaction with the pleats 402. For example, the sidewall 108 may include openings 126 located along the folding direction D at one or both ends of one or more of the pleats 402. Thus, air can flow through the openings 126 and then through the pleats 402 with relatively little impediment. The embodiment of FIG. 1 includes openings 126 at both ends of approximately half of the pleats 402, which is expected to significantly increase the deodorizing capacity of the air freshener medium as compared to a configuration in which the openings 126 are omitted.

In other embodiments, the body of the air freshener medium 114 may be provided in different forms. For example, rather than having a body comprising a pleated sheet, the body may comprise a foam material, a cloth material (e.g., a sheet or corrugated cloth), a sachet or bag, or the like. In each case, the odor treating chemicals may be impregnated into the material and/or contained within a receptacle within the material in solid, powder, gel or other form. In still other embodiments, the air freshener medium 114 may comprise a molded block of deodorizing compound, such as a block of air-dissolvable material containing the deodorizing compound. In still other embodiments, the air freshener medium 114 may comprise a liquid or gel that is retained in the frame 102 by vapor pervious sheets covering the openings 124, 126. Other alternatives and variations will be apparent to persons of ordinary skill in the art in view of the present disclosure.

As shown in FIG. 4A, the air freshener medium 114 comprises an opening 406 corresponding the passage 110. The opening 406 extends along the passage 110, and if the passage 110 includes a structure that extends into or through the enclosure, the opening 406 may surround that structure. The opening 406 may be made in any suitable way. In the case of the shown pleated air freshener medium 114, the opening 406 may be formed by die-cutting the air freshener medium 114 either before or after it is pleated. Alternatively, the opening 406 may be provided by perforations that user tears when installing the air freshener medium 114 into the frame 102, or the air freshener medium 114 may be provided with instructions for the user to cut it using a knife or scissors to fit over the passage 110. In other embodiments, the opening 406 may be molded or formed in place without requiring a separate step to remove it.

The opening 406 may be encircled by the air freshener medium 114, such as shown in FIG. 4A, but this is not strictly required. In other embodiments, the opening 406 may comprise a notch that extends to the outer perimeter of the air freshener medium 114, such that the air freshener medium 114 has a U-shape or the like.

In still other embodiments, the air freshener medium 114 may be provided as two or more parts that are placed in respective sides of the enclosure to surround or partially surround the passage. For example, as shown in FIG. 4B, the pleated sheet 400 may be split into two pieces 400*a*, 400*b*, one of which is placed on either longitudinal side of the passage 110. The two pieces 400*a*, 400*b* may remain spaced from each other when installed (i.e., they do not wrap around the passage 110 to touch each other), or they may be sized to wrap at least partially around the passage 110. Where the air freshener medium 114 is potentially subject to sliding or moving within the compartment formed by the frame 102, the frame 102 also may include locating ribs (not shown) or other structures to hold the air freshener medium 114 in place. For example, ribs may be provided to capture the portions of a split pleated sheet 400 in particular locations within the compartment, either by being located outside the perimeter of the sheet portions, or by fitting into the pleats. In this embodiment, the ribs 128 also may be reconfigured (e.g., widened) to fully cover any open space that might be present between the two pieces 400*a*, 400*b* of the pleated sheet 400. The use of separate pieces 400*a*, 400*b* also permits the two pieces 400*a*, 400*b* (or however many are used) to be made with different odor-reducing compositions, made with different constructions (e.g., a pleated sheet on one side and a block of deodorizing material on the other side), and so on. As another example, the enclosure can have one or more internal partitions to hold multiple similar or different air freshener media (e.g., one deodorizer medium, and one fragrance medium). Other alternatives and variations will be apparent to persons of ordinary skill in the art in view of the present disclosure.

Figure 5:
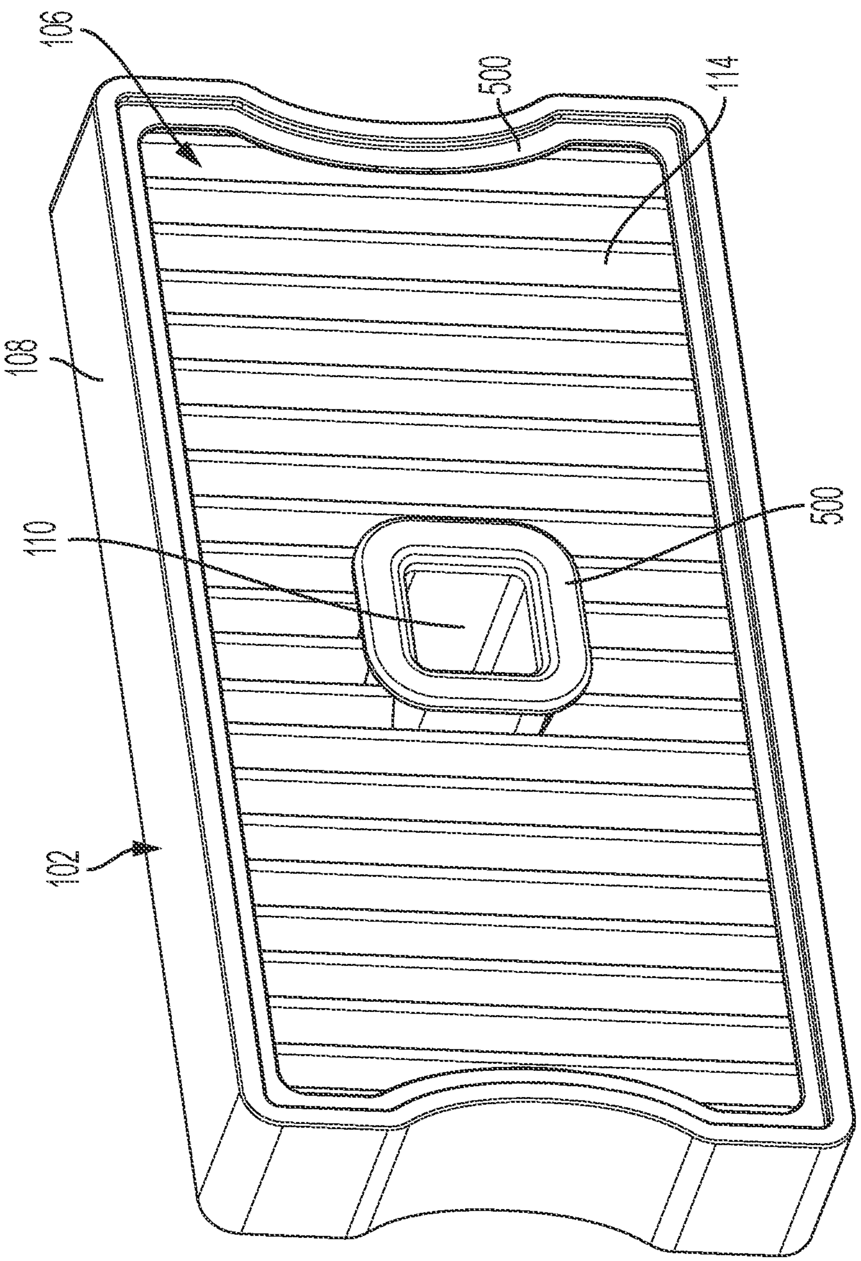
FIG. 5 shows an alternative exemplary embodiment of an air freshener.

FIG. 5 illustrates another exemplary embodiment, in which the frame 102 is essentially removed from the second face 106 to provide a larger air passage through the second face 106. Ribs 128 are provided on the first face 104 to hold the passage 110 in place, but are not provided on the second face 106. Thus, the second face 106 is reduced to a generally empty plane having portions of the frame 102 located only at the outer perimeter of the enclosure and at the passage 110. The air freshener medium 114 may be removable through the open second face 106. For example, narrow lips 500 may extend from the frame 102 and passage 110 to hold the outermost edge of the air freshener medium 114 during normal use, but when it is desired to change the air freshener medium 114, the air freshener medium 114 may be squeezed past the lip 500. Alternatively, the air freshener medium 114 may be permanently attached to the frame 102 by adhesives or the like.

FIG. 5 also shows an embodiment in which the frame 102 comprises a single unitary structure, such as a single molded plastic part. In this case, the passage 110 may comprise a unitary passage extending from the opening at the first face 104 to the opening at the second face 106.

Figure 6B:
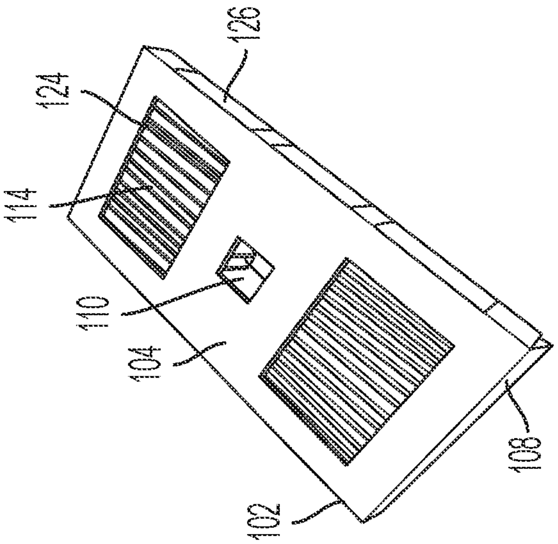
FIG. 6B shows another exemplary embodiment of an air freshener constructed with the frame of FIG. 6A.
Figure 6A:
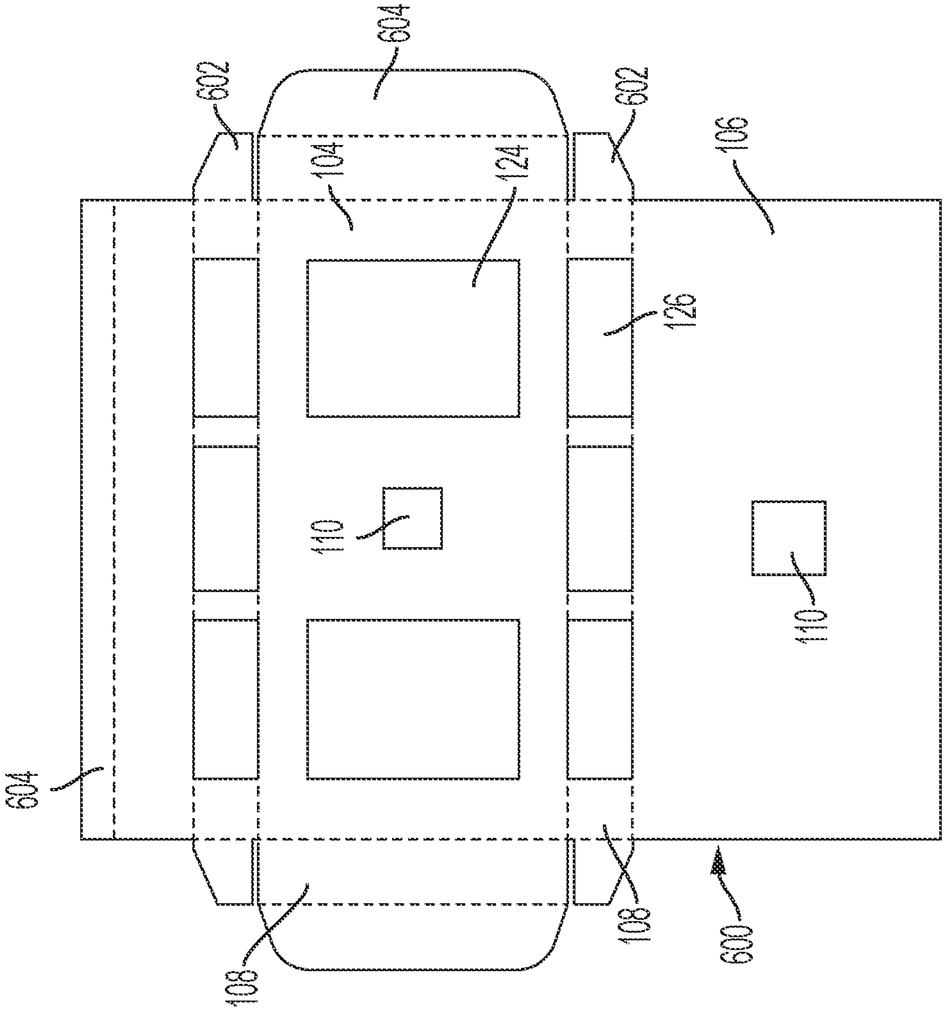
FIG. 6A show an alternative exemplary embodiment of an air freshener frame shown in a flat state.

FIGS. 6A and 6B show another embodiment, in which the frame 102 is formed by a sheet 600 of material, such as paper or cardboard. The sheet 600 is folded and secured to itself to form the frame 102 and enclosure. FIG. 6A shows the sheet 600 in a flat state, and FIG. 6B shows the sheet 600 folded to form the frame 102 and enclosure. As shown in FIG. 6A, the first face 104 is formed integrally with the second face 106 and sidewall 108. The sidewall 108 comprises multiple portions that are folded at 90 degrees to the first face 104 to form the perimeter of the enclosure. Integral tabs 602 may be included to form overlapping portions of the sidewall 108, to provide locations for gluing or otherwise bonding the sidewall portions together. The second face 106 is folded to be parallel to the first face 104 and cover the enclosure. Additional integral tabs 604 may be provided as locations to glue or attach the second face 106 to the sidewall 108. The first face 104 and sidewall 108 include openings 124, 126 to provide airflow to the air freshener medium. The first face 104 and the second face 106 also include respective openings to form two ends of the passage 110. In this case, the passage 110 extends along a passage axis from the first face 104 to the second face 106, but the passage is formed only as end segments defined by the openings through the first face 104 and the second face 106, and does not have a structure joining the first face 104 to the second face 106.

Figure 7B:
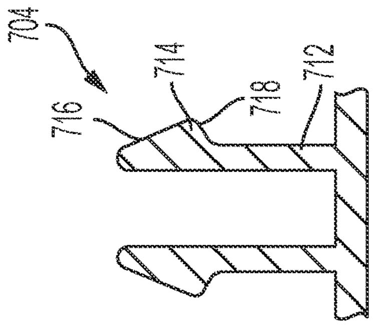
FIG. 7B shows a sectional side view of exemplary mounting posts of FIG. 7A.
Figure 7A:
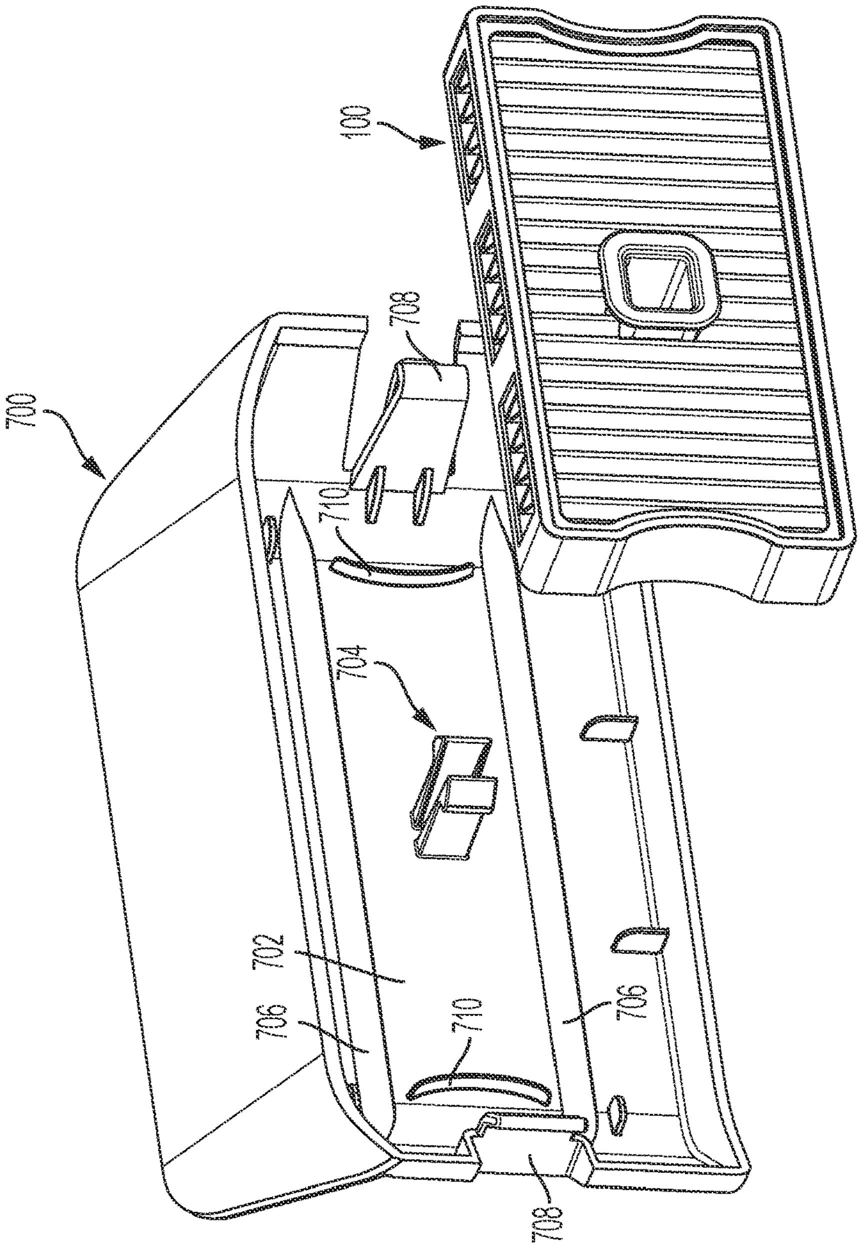
FIG. 7A shows an exemplary embodiment of an air freshener and cover.
Figure 8:
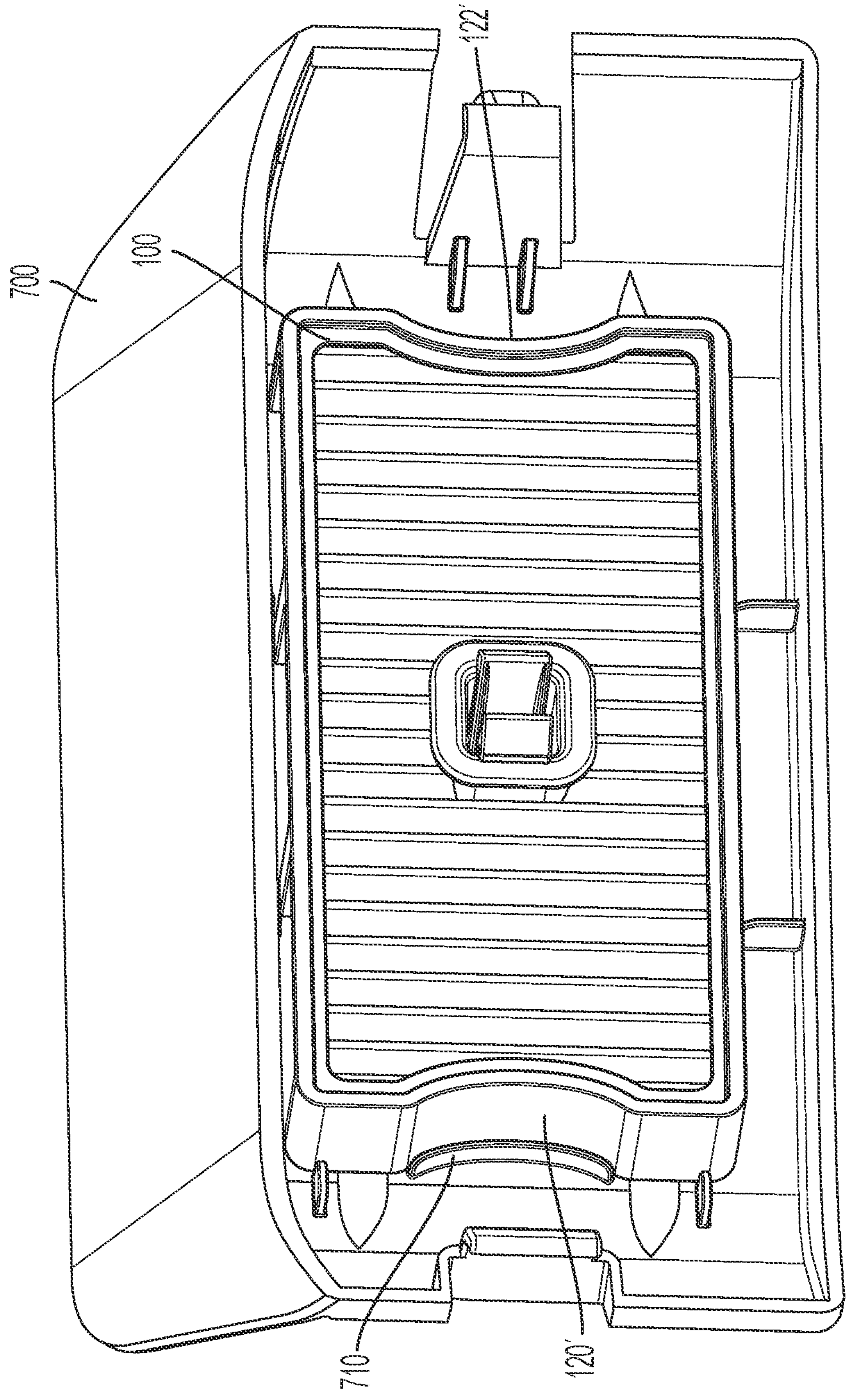
FIG. 8 shows the embodiment of FIG. 7 with the cover assembled with the air freshener.
Figure 9:
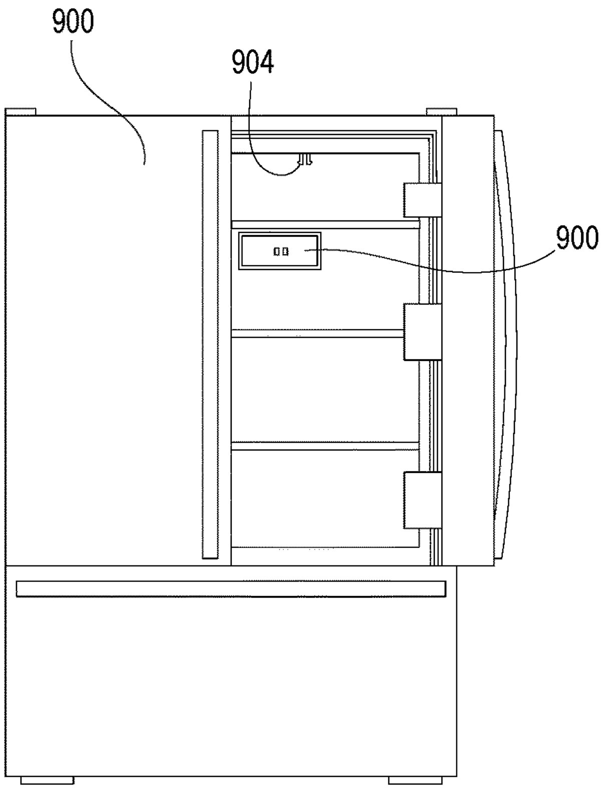
FIG. 9 shows an exemplary appliance having a mount for an air freshener.

Embodiments of air fresheners may be used on its own, in which case it is simply placed into a compartment or other space where the active compositions can remove odors or provide scents. More preferably, however, it is used in conjunction with a mounting system for securing the air freshener to the appliance. FIGS. 7 through 9 illustrate one example of an air freshener mounting system that is configured for use in a refrigerator or other appliance having a closable compartment or chamber. In this case, the air freshener 100 having a frame and air freshener medium (such as described above), is secured to a cover 700, and the cover 700 is secured to a mounting location within the appliance. It will be appreciated that the cover 700 may be omitted, and the securement made directly to the mounting location in the appliance, or other covers or mounting arrangements may be used.

The cover 700 has a cover body 702 and one or more posts 704 extending from the cover body. The posts 704 are configured to install in the passage 110 of the frame 102 to secure the frame 102 to the cover 700. The cover body 702 preferably is larger than the outer perimeter of the air freshener's enclosure, so as to wrap around at least part of the air freshener 100. Preferably, the cover body 702 is large enough to entirely surround the air freshener 100 as viewed along the passage axis 112. In the shown example, the air freshener 100 is elongated in a longitudinal direction, and the cover 700 is similarly elongated. When the air freshener 100 is attached to the cover 700, the cover body 702 surrounds the sides and one face of the air freshener 100, and the entire air freshener 100 may be within a volume formed by the cover body 702.

The cover body 702 may have one or more openings 706 passing therethrough to provide air ventilation through the cover 700 to the air freshener 100. However, such ventilation may be provided by air bypassing the outer edge of the cover body 702, or otherwise accessing the air freshener 100 without going through the cover 700.

The cover 700 also may include one or more connectors 708 configured to secure the cover 700 to a dedicated air freshener mount 900 located in an appliance 902 such as a refrigerator or freezer. The mount 900 may comprise, for example, a recess or surface that is shaped to receive the cover 700 and air freshener 100, and has connectors corresponding to those on the cover 700. In the shown example, the connectors 708 are spring clips, but other devices may be used. When installed, the cover 700 preferably holds the air freshener 100 in place, with the frame 102 between the cover body 702 and the air freshener mount 900.

The posts 704 (or post, if only one is used) are positioned relative to the passage 110 to ensure proper placement of the air freshener 100. In the shown example, the posts 704 are positioned to hold the air freshener 100 at a passage 110 located at the geometric center of the air freshener 100 as viewed along the passage axis 112. Additional supports to hold the air freshener 100 may also be provided. For example, as shown in FIG. 7, the cover body 702 may include one or more locating protrusions 710 that are positioned adjacent the frame 102 when the air freshener 100 is properly installed in the cover 700. In this example, the air freshener 100 is elongated and has concave curved end walls at its opposite longitudinal ends, such as described above, and the cover 700 has locating protrusions 710 in the form of arcuate ribs that fit within the concavity defined by the concave curved end walls of the air freshener 100. Each protrusion 710 is located outside the outer perimeter of the enclosure and may be slightly spaced from or in contact with the frame sidewall 108. Thus, the protrusions 710 provide support to prevent the air freshener 100 from rotating about the posts 702 or translating in the longitudinal direction of the air freshener 100. Other embodiments may use different locating protrusion 710, or the locating protrusions 710 may be omitted.

The posts 704 are configured to interact with the passage 110 to hold the air freshener 100 in place on the cover 700. In this example, each post 704 comprises a stem 712 that extends from the cover body 702, and a hook 714 that extends laterally (i.e. perpendicularly) from the stem 704. The hooks 714 of the two posts 704 extend in opposite lateral directions, to thereby extend away from one another. The stems 712 are dimensioned to fit within the passage 110, and the hooks 714 are dimensioned to wrap around a lip formed in or at the end of the passage 110. For example, the hooks 714 may wrap around the outer face of the passage 110 where it meets the first face 104 and the second face 106 (depending on which face 104, 106 is located away from the cover 700). In this example, the posts 704 extend all the way through the passage 110. In another example, the passage 110 may have an internal lip that the hooks 714 wrap around to hold the air freshener 100 in place, and in this case the posts 704 need not extend all the way through the passage.

The stems 712 are cantilevered from the cover body 702, and are flexible to allow the hooks 714 to move towards each other to install or remove the air freshener 100 from the cover 700. To assist with this movement during installation, one or both hooks 714 may have a beveled distal surface 716 that faces away from the cover body 702 and is sloped away from the stem 712 in the proximal direction (i.e., distal surface 716 is relatively close to the stem 712 at a point on the stem 712 that is more distant from the cover body 702, and relatively far from the stem 712 at a point on the stem 712 that is less distant from the cover body 702). Thus, applying a force to push the passage 110 onto the posts 704 will generate a corresponding force on the beveled distal surface 716 to move the posts 704 together to allow the hooks 714 to retract and enter the passage 110. Similarly, one or both hooks 714 may have a beveled proximal surfaces 718 that faces towards the cover body 702. The beveled proximal surfaces 718 are sloped to extend away from the stems 712 at greater distances from the cover body 702. Thus, a force to pull the air freshener 100 off of the posts 704 will generate a force on the beveled proximal surface 718 to retract the hooks 714.

The passage 110 also may be configured to help facilitate easy installation and removal of the air freshener 100 from the cover 700. For example, referring to FIG. 1, the passage 110 may terminate at the first face 104 at an opening 130 having a beveled entryway 132. The beveled entryway 132 extends towards the second face 106 (i.e., it sloped down towards the passage 110 in a direction towards the second face 106). Similarly, the passage 110 may terminate at the second face 106 at an opening having a beveled entryway that extends towards the first face 104 (the second face 106 in this respect may be a essentially identical or a mirror image of the first face 104, thus the illustration of the beveled entryway 132 and opening 130 on the first face 104 also illustrates and example of a beveled entryway and opening on the second face 106). The beveled entryways 132 act similarly to the beveled distal surfaces 716 and beveled proximal surfaces 718 described above. Specifically, the beveled entryways 132 convert a portion of a force installing or removing the air freshener 100 into a lateral force to compress the posts 704 together.

It will be appreciated that embodiments may include beveled surfaces 716, 718 on the hooks 714, and the beveled entryways 132, to make installation and removal easier. However, other embodiments may omit one or more of the beveled surfaces 716, 718 and beveled entryways 132. For example, where it is desired to make removal of the air freshener more difficult (e.g., to prevent accidental release), the beveled proximal surfaces 718 and beveled entryways 132 may be replaced by surfaces that extend perpendicular to the passage axis 112. In such case, the air freshener 100 may be removable by manually squeezing the posts 704 together to release the hooks 714. Other alternatives and variations will be apparent to persons of ordinary skill in the art in view of the present disclosure.

The foregoing embodiment uses two posts 704 that have oppositely-directed snap fit connectors that engage the passage 110 to hold the air freshener 100 in place on the cover 700. This arrangement, along with the symmetrical configuration of the air freshener 100, allows the air freshener 100 to be installed in as many as four different orientations on the cover 700 (i.e., first face 104 facing the cover body 702; first face 104 facing the cover body 702 with the air freshener 100 rotated 180 degrees about the passage axis 112; second face 106 facing the cover body 702; and second face 106 facing the cover body 702 with the air freshener 100 rotated 180 degrees about the passage axis 112). Although desirable in this embodiment, this installation flexibility is not strictly required.

Other embodiments also may use different arrangements of posts. For example, the two posts 704 may be replaced by a single post having a movable or removable fastener (e.g., a pivoting catch, a screw, a twist-lock fitting, etc.) that is moved aside or removed to install or remove the air freshener 100. The posts 704 also may comprise more than two posts, such as three posts to engage a triangular passage 110. Other alternatives and variations will be apparent to persons of ordinary skill in the art in view of the present disclosure.

In still other embodiments, the posts 704 or other mounting mechanisms or structures may be provided on something other than a cover 700. For example, the posts 704 may protrude directly from an inner wall of a refrigerator cabinet, as shown by the mounting posts 904 in FIG. 9. In such a configuration, an additional cover (not shown) may be provided to attach over the air freshener, such as by attaching the cover to the wall or to the air freshener. Alternatively, the air freshener may have an integral cover formed as part of or permanently attached to the frame. For example, one face 104, 106 may be formed as a solid or mostly solid wall, which may be shaped to blends into the surrounding portions of the cabinet wall to provide a desirable aesthetic appearance. As another alternative, no cover may be provided over the air freshener.

FIGS. 10A-10E show various exemplary embodiments for connecting the air freshener passage 110 and the mounting post or posts 704 (which may be in the cover 700, or extend from a cabinet wall or the like).

Figure 10A:
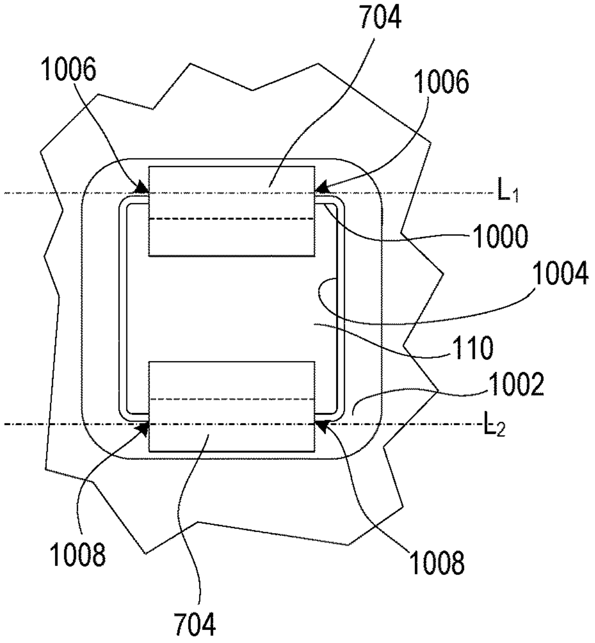
FIGS. 10A-10F show exemplary embodiments of passages through air fresheners and mounting posts for retaining the air freshener using the passage.

FIG. 10A shows the embodiment of FIG. 1 as viewed along the passage axis 112. Here, it can be seen that the passage 110 has a first perimeter portion 1000 and a second perimeter portion 1002 facing and parallel to the first perimeter portion 1000. The posts 704 extend in the passage 110, with one post 704 positioned adjacent to the first perimeter portion 1000 and the other post positioned adjacent to the second perimeter portion 1002 when the frame is secured to the posts 704. In this case, the first perimeter portion 1000 and second perimeter portion 1002 face one another and are parallel to one another. Sidewalls 1004 may be provided to join the first perimeter portion 1000 to the second perimeter portion 1002, and thereby enclose the passage 110. The sidewalls 1004 in this example are also straight and parallel to one another, and extend perpendicular to the first and second perimeter portions 1000, 1002, making the passage a rectangular or square shape as viewed along the passage axis 112.

It will be appreciated that the passage and posts can have alternative shapes and configurations. For example, the passage may be triangular, and three posts may be provided in a matching triangular shape. As another example, the passage and post may have matching circular shapes or other matching shapes.

It will also be appreciated that embodiments may include passages that are not rectangular, but nevertheless can properly engage the posts 704 as described above. FIGS. 10B-F show examples of such passage shapes.

Figure 10B:
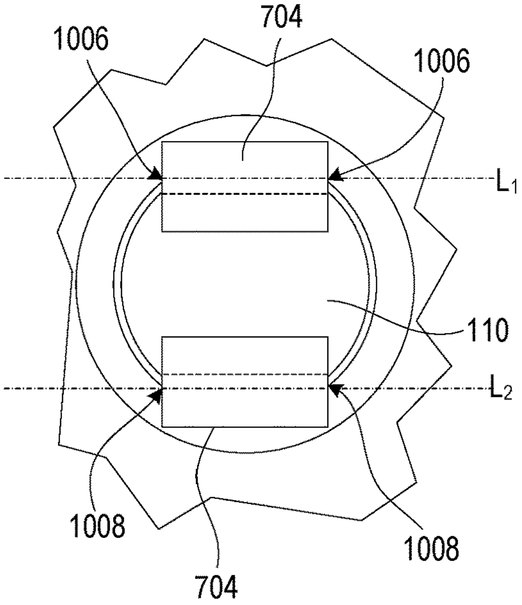
Figure 10C:
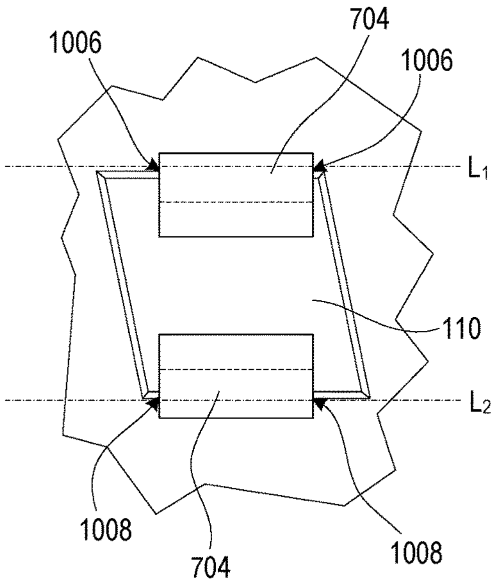
Figure 10D:
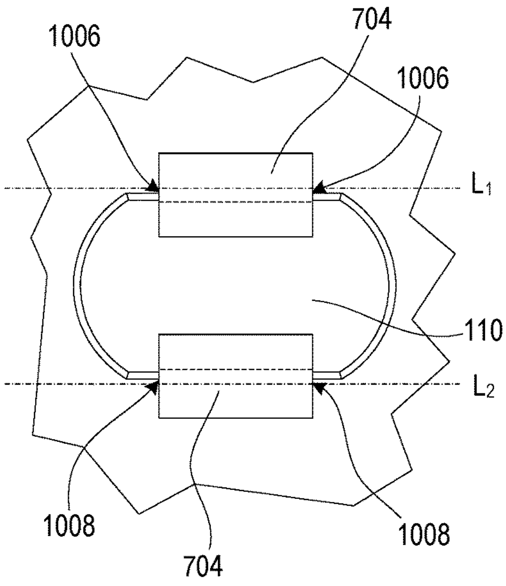
Figure 10E:
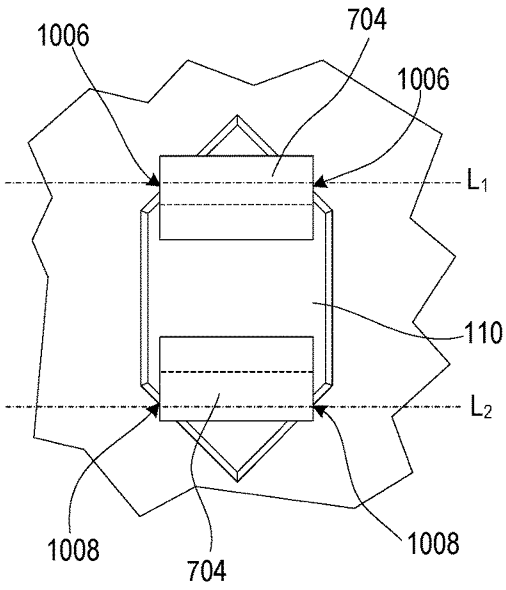
Figure 10F:
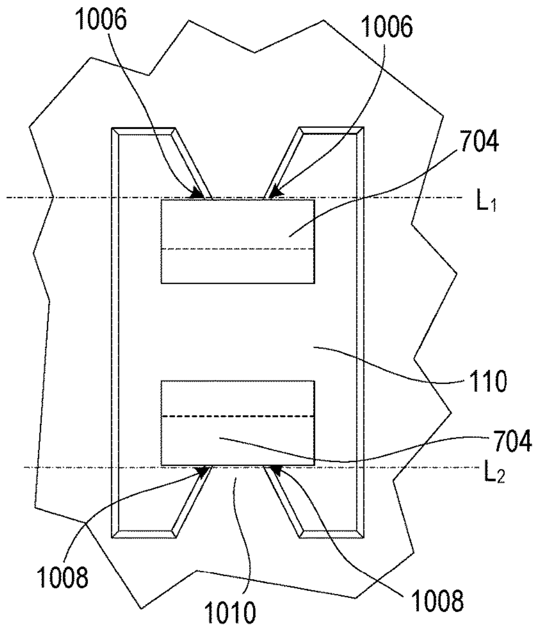

In FIG. 10B, the passage 110 ends at a circular opening that surrounds the passage 110. In FIG. 10C, the passage 110 ends at a parallelogram-shaped (or trapezoidal) opening that surrounds the passage 110. In FIG. 10D, the passage 110 ends at an opening having a "pill" shape having parallel facing surfaces joined by curved surfaces (the pill shape may be oriented as shown, or at 90 degrees or other angles to the shown example). In FIG. 10E, the passage 110 ends at an opening having a rectilinear shape in the form a "picket" having two parallel side walls joined by V-shaped end walls. In FIG. 10F, the passage 110 ends at an opening having an "H" or "dogbone" shape, having two opposed convex end walls that protrude into the passage 100, and straight walls joining the convex walls.

In each case, when the air freshener 100 is installed on the posts 704, portions of the passage 110 perimeter lie under the hooks 714 at four or more discrete points. Two points 1006 lie under the hook 714 of one post 704, and two points 1008 lie under the hook 714 of the other post 704. Each pair of points 1006, 1008 is arranged on or near respective line $L_1$, $L_2$. The lines $L_1$, $L_2$ are parallel to one another, and the stems 712 of the posts 704 are located between the lines. Thus, all of the foregoing shapes (and others having appropriate point locations) can operate with the posts 704 to retain the air freshener 100 in place. It will appreciated that the shape of the passage perimeter can be modified to reduce the spacing between the points 1006, 1008. For example, in the embodiment of FIG. 10F, one of the dogbone protrusions 1010 may be made very narrow so as to move points 1008 close together. It will also be appreciated that one or more of the points 1006, 1008 may not be a contact point between the hooks 714 and the air freshener 100. For example, the perimeter of the passage 110 may have undulations or recesses that form a gap between the frame 102 and the hooks 714 at one or more of the points 1006, 1008. Other alternatives and variations will be apparent to persons of ordinary skill in the art in view of the present disclosure.

The present disclosure describes a number of inventive features and/or combinations of features that may be used alone or in combination with each other or in combination with other technologies. The embodiments described herein are all exemplary, and are not intended to limit the scope of the claims. It will also be appreciated that the inventions described herein can be modified and adapted in various ways, and all such modifications and adaptations are intended to be included in the scope of this disclosure and the appended claims.

The invention claimed is:

1. An appliance air freshener comprising:

an enclosure frame having a top wall comprising one or more top wall openings defined therein, a bottom wall comprising one or more bottom wall openings defined therein, and side walls extending between the top and bottom walls, wherein:

the side walls define an outer perimeter of the enclosure frame and comprise a first end wall, a second end wall, a front wall between the first and second end walls, and a rear wall between the first and second end walls, and one or more front wall openings formed in the front wall are located opposite one or more rear wall openings formed in the rear wall; and an air freshener medium, located within the enclosure frame, comprising a sheet having a plurality of folds defining a plurality of pleats, wherein:

the folds comprise regions of the sheet folded about respective fold axes, each of the fold axes extends across the enclosure frame from the front wall to the rear wall, the one or more top wall openings substantially expose an entire top surface of the air freshener medium, the sheet comprises paper, a woven fabric, or a non-woven fabric, and the sheet is impregnated with one or more of: sodium bicarbonate or activated charcoal.

2. The appliance air freshener of claim 1, wherein each of the front and rear walls is longer than each of the first and second end walls.

3. The appliance air freshener of claim 1, wherein opposite edges of the air freshener medium sheet, located adjacent to interior surfaces of the front and rear walls, comprise peaks and valleys defined by the plurality of folds.

4. The appliance air freshener of claim 1, wherein the air freshener medium is exposed by the one or more bottom wall openings, by the one or more front wall openings, and by the one or more rear wall openings.

5. The appliance air freshener of claim 1, wherein the enclosure frame and the air freshener medium define:

a plurality of air flow channels from the one or more bottom wall openings, along the plurality of pleats, and out the one or more front wall openings, a plurality of air flow channels from the one or more bottom wall openings, along the plurality of pleats, and out the one or more rear wall openings, a plurality of air flow channels from the one or more top wall openings, along the plurality of pleats, and out the one or more front wall openings, and a plurality of air flow channels from the one or more top wall openings, along the plurality of pleats, and out the one or more rear wall openings.

6. The appliance air freshener of claim 1, wherein each of the fold axes is perpendicular to the front and rear walls.

7. The appliance air freshener of claim 1, wherein each of the first end wall and the second end wall comprises a concave curved outer surface.

8. The appliance air freshener of claim 1, wherein the enclosure frame comprises a unitary plastic structure.

9. The appliance air freshener of claim 1, wherein the enclosure frame comprises a housing portion and a lid portion that are configurable between a closed position in which the air freshener medium is retained in the enclosure frame, and an open position in which the air freshener medium is removable from the enclosure frame.

10. The appliance air freshener of claim 9, wherein the enclosure frame comprises a unitary plastic structure, and the housing portion is attached to the lid portion by a unitary hinge.

11. An appliance air freshener comprising:

an enclosure frame having a top wall comprising one or more top wall openings defined therein, a bottom wall comprising one or more bottom wall openings defined therein, and side walls extending between the top and bottom walls, wherein:

the side walls define an outer perimeter of the enclosure frame and comprise a first end wall, a second end wall, a front wall between the first and second end walls, and a rear wall between the first and second end walls, and one or more front wall openings formed in the front wall are located opposite one or more rear wall openings formed in the rear wall; and an air freshener medium, located within the enclosure frame, comprising a sheet having a plurality of folds defining a plurality of pleats, wherein:

the folds comprise regions of the sheet folded about respective fold axes, each of the fold axes extends across the enclosure frame from the front wall to the rear wall, the one or more top wall openings substantially expose an entire top surface of the air freshener medium, and the enclosure frame comprises a passage defined by a first passage opening in the top wall and a second passage opening in the bottom wall, the passage is located within and spaced apart from the outer perimeter, the passage extends from an outer face of the top wall to an outer face of the bottom wall, and the air freshener medium is absent from the passage.

12. The appliance air freshener of claim 11, wherein each of the front and rear walls is longer than each of the first and second end walls.

13. The appliance air freshener of claim 11, wherein each of the first end wall and the second end wall comprises a concave curved outer surface.

14. The appliance air freshener of claim 11, wherein the enclosure frame comprises a unitary plastic structure.

15. An appliance air freshener comprising:

an enclosure frame having a top wall comprising one or more top wall openings defined therein, a bottom wall comprising one or more bottom wall openings defined therein, and side walls extending between the top and bottom walls, wherein:

the side walls define an outer perimeter of the enclosure frame and comprise a first end wall, a second end wall, a front wall between the first and second end walls, and a rear wall between the first and second end walls, and one or more front wall openings formed in the front wall are located opposite one or more rear wall openings formed in the rear wall; and an air freshener medium, located within the enclosure frame, comprising a sheet having a plurality of folds defining a plurality of pleats, wherein:

the folds comprise regions of the sheet folded about respective fold axes, each of the fold axes extends across the enclosure frame from the front wall to the rear wall, the pleats extend substantially from an interior surface of the bottom wall to an interior surface of the top wall, a length of a top wall opening, of the one or more top wall openings, in a direction parallel to the front wall is at least approximately one half of a length of the enclosure frame, a width of the top wall opening in a direction perpendicular to the front wall is at least approximately one half of a width of the enclosure frame, the sheet comprises paper, a woven fabric, or a non-woven fabric, and the sheet is impregnated with one or more of: sodium bicarbonate or activated charcoal.

16. The appliance air freshener of claim 15, wherein each of the front and rear walls is longer than each of the first and second end walls.

17. The appliance air freshener of claim 15, wherein the air freshener medium is exposed by the one or more top wall openings, by the one or more bottom wall openings, by the one or more front wall openings, and by the one or more rear wall openings.

18. The appliance air freshener of claim 15, wherein the enclosure frame comprises a passage defined by a first passage opening in the top wall and a second passage opening in the bottom wall, the passage is located within and spaced apart from the outer perimeter, the passage extends from an outer face of the top wall to an outer face of the bottom wall, and the air freshener medium is absent from the passage.

19. An appliance air freshener comprising:

an enclosure frame having a top wall comprising one or more top wall openings defined therein, a bottom wall comprising one or more bottom wall openings defined therein, and side walls extending between the top and bottom walls, wherein:

the side walls define an outer perimeter of the enclosure frame and comprise a first end wall, a second end wall, a front wall between the first and second end walls, and a rear wall between the first and second end walls, and one or more front wall openings formed in the front wall are located opposite one or more rear wall openings formed in the rear wall; and an air freshener medium, located within the enclosure frame, comprising a sheet having a plurality of folds defining a plurality of pleats, wherein:

the sheet is impregnated with one or more of: sodium bicarbonate or activated charcoal; and the one or more top wall openings substantially expose an entire top surface of the air freshener medium.

20. The appliance air freshener of claim 19, wherein each of the front and rear walls is longer than each of the first and second end walls.

21. The appliance air freshener of claim 19, wherein the sheet comprises paper, a woven fabric, or a non-woven fabric.

22. The appliance air freshener of claim 19, wherein the enclosure frame comprises a passage defined by a first passage opening in the top wall and a second passage opening in the bottom wall, the passage is located within and spaced apart from the outer perimeter, the passage extends from an outer face of the top wall to an outer face of the bottom wall, and the air freshener medium is absent from the passage.

* * * * *